(12) United States Patent
O'Donnell et al.

(10) Patent No.: US 6,254,582 B1
(45) Date of Patent: *Jul. 3, 2001

(54) ABSORBENT PRODUCT PROVIDED IN ROLL FORM

(75) Inventors: Kathleen Denise O'Donnell, Somerville; Thomas Joseph Luceri, Neshanic Station, both of NJ (US)

(73) Assignee: McNeil-PPC, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/012,767

(22) Filed: Jan. 23, 1998

Related U.S. Application Data

(63) Continuation of application No. 08/006,593, filed on Jan. 21, 1993, now abandoned.

(51) Int. Cl.[7] .................................................. A61F 13/15
(52) U.S. Cl. ................................ 604/385.05; 604/385.05; 604/387
(58) Field of Search ................... 128/849; 602/41–47, 602/52–59, 900, 903; 604/364–366, 373–377, 379–383, 385.1–387, 389–396, 385.01, 385.03, 385.11, 385.14, 385.05; 206/389–390, 398, 403, 410, 411, 412; 428/43; 162/114, 194

(56) References Cited

U.S. PATENT DOCUMENTS

| | | |
|---|---|---|
| 1,238,356 | 8/1917 | Stokes . |
| 2,331,271 | 10/1943 | Gilchrist . |
| 2,399,545 | 4/1946 | Davis . |
| 2,508,855 | 5/1950 | Brown . |
| 3,049,228 | 8/1962 | Burnett . |

(List continued on next page.)

FOREIGN PATENT DOCUMENTS

| | | |
|---|---|---|
| 435 550 | 10/1967 | (CH) . |
| 0241041 | 10/1987 | (EP) . |
| 2 541 247 | 8/1984 | (FR) . |
| 1331354 | 9/1973 | (GB) . |
| 2 141 396 | 12/1984 | (GB) . |
| 219596 | 1/1990 | (JP) . |
| 9210984 | 7/1992 | (WO) . |

*Primary Examiner*—Aaron J. Lewis
*Assistant Examiner*—K. M. Reichle

(57) ABSTRACT

A supply of absorbent panty liner pads formed by a contiguous longitudinal array of pad segments forming a strip. The strip has locally weakened zones to facilitate tearing off segments from the strip without the use of a cutting tool. Each pad segment is shorter than a standard panty liner pad so that approximately three segments are required to form a standard length pad. By tearing off two, three, four, or five segments in one piece, the user can create a panty liner having a short, standard, long or extra long length to suit her needs on any given day. The strip is wrapped upon itself into a roll so that pressure sensitive positioning adhesive strips are placed into contact with release surfaces formed on the strip, thereby protecting the adhesive prior to use without the need for release paper.

15 Claims, 3 Drawing Sheets

U.S. PATENT DOCUMENTS

| | | |
|---|---|---|
| 3,071,138 | 1/1963 | Garcia . |
| 3,143,208 | 8/1964 | Sizemore, Jr. . |
| 3,183,910 | 5/1965 | Patterson . |
| 3,211,147 | 10/1965 | Pherson et al. . |
| 3,315,676 | 4/1967 | Cooper . |
| 3,411,504 | 11/1968 | Glassman . |
| 3,638,651 | 2/1972 | Torr . |
| 3,828,784 | 8/1974 | Zoephel . |
| 3,835,992 | 9/1974 | Adams, IV. . |
| 3,885,566 | 5/1975 | Jacob . |
| 3,916,447 | 11/1975 | Thompson . |
| 3,943,930 | 3/1976 | Schaar . |
| 3,967,622 | 7/1976 | Cepuritis . |
| 4,097,943 | 7/1978 | O'Connell . |
| 4,194,507 | 3/1980 | Ness et al. . |
| 4,245,630 | 1/1981 | Lloyd et al. . |
| 4,327,732 | 5/1982 | Thinnes . |
| 4,427,737 | 1/1984 | Cilento et al. . |
| 4,505,704 | 3/1985 | Roeder . |
| 4,562,102 | 12/1985 | Rabuse et al. . |
| 4,598,528 | 7/1986 | McFarland et al. . |
| 4,605,404 | 8/1986 | Sneider . |
| 4,770,298 | 9/1988 | McFarland et al. . |
| 4,772,499 | 9/1988 | Greenway . |
| 4,773,905 | 9/1988 | Molee et al. . |
| 4,946,454 | 8/1990 | Schmidt . |

ABSORBENT PRODUCT PROVIDED IN ROLL FORM

RELATED APPLICATIONS

This application is a continuation of U.S. Ser. No. 08/006,593 filed Jan. 21, 1993, now abandoned.

FIELD OF THE INVENTION

The current invention is directed to absorbent products such as panty liners, sanitary napkins, incontinence pads and the like. More specifically, the current invention is directed to an absorbent product provided in roll form that is segmented to allow the user to customize the length of the product and that eliminates the need for release paper.

BACKGROUND OF THE INVENTION

In the past, absorbent pads such as panty liners, sanitary napkins and incontinence pads have been sold in fixed lengths. Typically, the user will desire a longer length on those days when she expects a large flow and a shorter length when she expects a small flow. However, absorbent pads are generally sold in only two predetermined lengths—standard and long. Consequently, a user whose needs could be optimally met by a pad having an intermediate length between standard and long, or by a very short or very long pad, will have to settle for a pad having less than optimal length. Moreover, even if the user finds that "standard" and "long" pads are of suitable length, she must still purchase and store both types so that the appropriate pad can be selected on any given day.

Consequently, it would be desirable to provide an absorbent pad in a continuous strip, preferably in roll form, in such a manner that the user could readily customize the pad length to her individual needs on any given day.

Past approaches to providing absorbent pads in roll form have not been entirely adequate. Generally, such rolls contain pads of fixed length, offering the user no more flexibility in terms of pad length than when buying individual pads. Illustrative of this approach are U.S. Pat. Nos. 3,183,910 (Patterson) and 4,598,528 (McFarland). Another approach, disclosed in U.S. Pat. No. 4,505,704 (Roeder), allows the user to cut the rolled pad into any desired length. However, it is necessary to either supply the roll in a dispenser having a cutting edge, or to instruct the user to employ scissors to cut the roll into individual pads of the desired length.

Consequently, it would be desirable to provide a pad in roll form that could be divided into pads of various lengths without requiring the user to carry about a special dispenser or a pair of scissors.

Another problem associated with traditional absorbent pads arises because they are generally held in place by pressure sensitive adhesive, typically a double sided tape or a hot melt type glue, disposed on the garment facing side of the pad. The pressure sensitive adhesive holds the pad in place by adhering it to the crotch of the wearer's undergarment. The pressure sensitive adhesive is covered with release paper that protects the adhesive from dirt and unintended adhesion during manufacture, packaging and storage. Since the release paper must be removed by the user just prior to application of the product to an undergarment, its presence creates waste and complicates the utilization of the product.

Consequently, it would be desirable to provide an absorbent pad in roll form that utilized pressure sensitive adhesive strips for pad placement but that did not require release paper.

SUMMARY OF THE INVENTION

It is an object of the current invention to provide an absorbent pad in roll form that can be divided into pads of various lengths, without requiring the user to carry about a special dispenser or a pair of scissors, and that utilized pressure sensitive adhesive for pad placement but that did not require release paper to protect the adhesive. These and other objects are accomplished in a strip of absorbent product from which individual absorbent pads may be torn, comprising (i) longitudinally extending body facing and garment facing surfaces formed on opposing sides of the absorbent product strip, (ii) a longitudinally extending strip of absorbent material having a length, a width, and first and second longitudinally extending surfaces, and (iii) a longitudinally extending fluid impervious barrier strip, at least a portion of the barrier strip covering the first surface of the absorbent material strip and forming the garment facing surface. The strip of absorbent material has a plurality of weakened zones. The weakened zones are arranged along lines extending substantially transversely across the width of the absorbent material strip so as to form preferential tearing lines. The tearing lines are spaced at predetermined intervals along the length of the absorbent material strip so to form strip segments.

In one embodiment of the current invention, the absorbent product strip is formed into a roll by wrapping the absorbent material strip, with the barrier strip covering the first surface, onto itself so as to bring the body facing surface into contact with the garment facing surface. In this embodiment, the strip of absorbent product further comprises (i) a strip of pressure sensitive adhesive disposed on the garment facing surface, and (ii) a release surface formed on the body facing surface. When the absorbent product strip is wrapped into the roll, the strip of pressure sensitive adhesive is brought into contact with the release surface, thereby protecting the adhesive.

The current invention also encompasses a method of making absorbent pads for use in absorbing body fluids so as to prevent staining of a user's garment. In one embodiment of the method, the absorbent pads are made by the steps of (i) forming a longitudinally extending strip of absorbent material having a length and a width, (ii) forming a plurality of weakened zones in the strip of absorbent material, the weakened zones arranged along lines extending substantially transversely across the width of the strip of absorbent material so as to form preferential tearing lines, the tearing lines spaced at predetermined intervals along the length of the strip of absorbent material so as to define strip segments therebetween, and (iii) tearing a plurality of contiguous strip segments from the absorbent material strip by tearing along one of the weakened zones so as to form an absorbent pad formed by the plurality of contiguous strip segments.

Accordingly, the claimed invention relates to a supply of absorbent pads for use in absorbing body fluids so as to prevent staining of a user's garment, comprising a longitudinally extending strip of absorbent pad segments, the pad segments having a predetermined uniform interval length of from about 1 to about 3 inches said strip being tearable into individual absorbent pads without the use of a dispenser having a cutting edge or scissors, said strip of absorbent pad segments having longitudinally extending first and second edges and: a) a longitudinally extending body facing surface defined in part by a first major surface of a longitudinally extending strip of absorbent material having a plurality of substantially transverse weakened zones forming preferential tearing lines, said weakened zones spaced at predetermined intervals along said absorbent material strip corresponding to the predetermined interval lengths of said pad segments; (b) a longitudinally extending fluid impervious barrier strip, wherein a portion of said barrier strip overlies and is adhesively bonded to the absorbent material covering a second major surface, opposite the first major surface of said absorbent material strip and forming a longitudinally extending garment facing surface of said strip of absorbent pad segments, and portions of said barrier strip forming first and second portions of said body facing surface adjacent said first and second longitudinally extending edges, respectively; (c) a pressure sensitive adhesive disposed on said garment-facing surface of said strip of the absorbent pad segments; and (d) a continuous, longitudinally extending release surface formed on said first and second portions of said body-facing surface formed by said barrier strip, proximate the edges; wherein said fluid impervious barrier strip forms a fluid barrier which prevents fluid leakage during use of said absorbent pads, said longitudinally extending strip of absorbent pad segments is wrapped around itself into a roll to place said pressure sensitive adhesive into contact with at least a portion of said release surface and said individual absorbent pads are formed of a plurality of absorbent pad segments.

The claimed invention also relates to a method of making absorbent pads, comprising the steps of: (a) forming a longitudinally extending strip of an absorbent element, said absorbent element having first and second opposed longitudinally extending surfaces, longitudinally extending edges, and a plurality of substantially transverse weakened zones forming preferential tearing lines, said weakened zones spaced at predetermined, uniform intervals about 1 to about 3 inches along said absorbent element to define absorbent pad segments therebetween; (b) overlaying said second surface, said longitudinally extending edges, and a portion of said first surface, with a fluid impervious barrier strip; (c) depositing a pressure sensitive adhesive on at least a portion of said barrier strip overlaying said second surface; (d) forming a release surface on at least a portion of said barrier strip overlaying said portion of said first surface; and (e) wrapping said strip of absorbent element around itself into a roll so as to place said pressure sensitive adhesive into contact with at least a portion of said release surface.

DESCRIPTION OF THE PREFERRED EMBODIMENT

Figure 1:
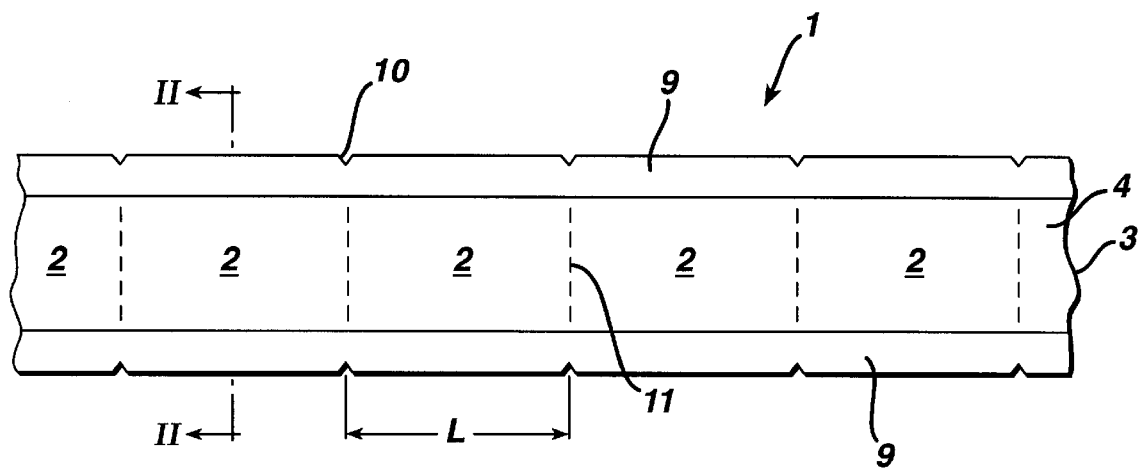
FIG. 1 is plan view of the absorbent product strip of the current invention prior to being wrapped into roll.
Figure 2:
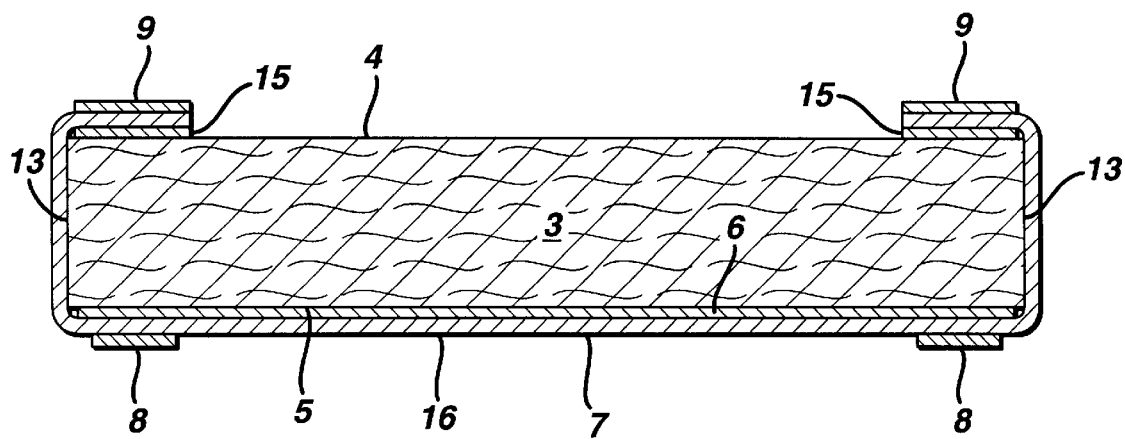
FIG. 2 is a cross-section taken through lines II—II, shown in FIG. 1.

A supply of panty liner pads, provided in a strip 1 according to the current invention, is shown in FIGS. 1 and 2. As shown best in FIG. 2, the panty liner supply strip 1 is comprised of a longitudinally extending strip of an absorbent material 3 and a longitudinally extending barrier strip 7. The absorbent strip 3 has an upper surface 4, which forms a portion of the body facing surface of the product in use, and a lower surface 5. In the preferred embodiment, the absorbent strip 3 is a non-woven fusible fiber pulp fabric available from Personal Products Co. of Miltown, N.J., or HILOFT fabric, a pulp fabric available from Scott Paper Company.

As shown in FIG. 2, the entirety of the lower surface 5 of the absorbent strip 3 is covered by a longitudinally extending fluid impervious barrier 7. The barrier 7 forms the garment facing surface 16 of the product in use. The barrier 7 is attached to the lower surface 5 of the absorbent strip by means of a layer of adhesive 6, such as Scotch SPRA-MENT adhesive, available from 3-M Company, St. Paul, Minn. In the preferred embodiment, the barrier 7 is formed from a 1.35 mil thick layer of 40% high density and 60% low density polyethylene. Suitable barrier films are available from Banner Packaging Inc., Winnenbago, Wis.

The barrier 7 could also be formed from a polytetraflouroethylene (TEFLON) film. Such a film would not require a release coating to form a release surface since it inherently forms a low bond strength with adhesives. However, in such cases, the barrier film would have to be treated on the garment facing side to ensure that the adhesive remained in place.

In addition to covering the lower surface 5 of the strip of absorbent material 3, the barrier 7 is wrapped around the longitudinally extending edges 13 of the absorbent strip 3 and the portions of its upper surface 4 adjacent each of the edges 13, as shown in FIG. 2. By covering the edges 13 of the absorbent strip 3, the barrier 7 prevents side leakage of fluid that might stain the user's undergarment. By covering portions of the upper surface 4 of the absorbent strip 3, the barrier 7 creates a surface on which a release surface can be formed, as discussed further below. The barrier 7 is attached to the upper surface 4 of the absorbent strip 3 by means of a strip of adhesive 15, such as Fuller L-3585, available from, H.B. Fuller Co., St. Paul, Minn.

As is well known in the art, panty liner pads are utilized by attaching them to the crotch portion of the user's undergarment using a positioning adhesive. Consequently, pressure sensitive adhesive 8 is applied to the barrier 7 adjacent each of the edges 13 of the absorbent strip 3. In the preferred embodiment, the adhesive 8 is applied in continuous, longitudinally extending strips that run the length of the absorbent strip 3. However, as those skilled in the art will readily appreciate, the adhesive 8 could also be applied in intermittent strips, patches or a variety of other patterns. In the preferred embodiment, the pressure sensitive adhesive is of the hot melt type, such as an A-B-A block copolymer (i.e., styrene-ethylene-butylene-styrene block copolymer). By way of example, the pressure sensitive adhesive may be Fuller HM-6514, available from, H.B. Fuller Co., St. Paul, Minn., applied at approximately 74 mg/in$^2$. Alternatively, a double sided adhesive tape could be utilized. As will be discussed further below, according to the current invention, no release paper is necessary to protect the pressure sensitive adhesive 8 prior to application of the panty liner pad to the undergarment.

As shown in FIGS. 1 and 2, a release surface 9 is formed on the portions of the barrier 7 that cover the portions of the upper surface 4 of the adhesive strip 3 adjacent its edges 13. In the preferred embodiment, the release surface is formed by coating the portions of the barrier 7 with silicone prior to joining the barrier to the absorbent strip 3. The silicone coating is deposited in a continuous, longitudinally extending strip and may be applied by a variety of methods, such as direct or reverse gravure coaters or ink jet printing. After it is applied to the barrier film 7, the silicone coating may be cured, such as by ultraviolet curing, heat curing or electron beam curing. Suitable coating can be performed by Release Technologies of Chicago, Ill.

As shown in FIG. 1, according to an important aspect of the current invention, the supply strip of panty liners 1 is formed by a number of contiguous segments 2 arranged longitudinally along the length of the strip. Each segment 2 is delineated from the adjacent segments by preferential tear lines 11 that extend transversely across the width of the absorbent strip 3, as shown in FIG. 1. The tear lines 11 are formed by locally weakening the absorbent strip 3. In the preferred embodiment, the tear lines 11 are formed by perforating the absorbent strip 3. As a result of this localized weakening of the strip 3, the application of sufficient tearing force to the absorbent strip will cause a segment to separate from the strip at a tear line 11 between segments, rather than tearing within a segment.

In the preferred embodiment, preferential tearing along lines 11 is further enhanced by the formation of notches 10 in the portions of the barrier 7 covering each of the sides 13 of the absorbent strip 3. In the preferred embodiment, the notches 10 are formed by cutting slits in the barrier 7. As shown in FIG. 1, the notches 10 in the barrier 7 are longitudinally aligned with the tear lines 11 in the absorbent strip 3. The notches 10 act to concentrate the stress applied to the panty liner supply strip 1 when a segment 2 is torn off, thereby facilitating the fracture of the barrier 7 at the notch 10 location. Since, as discussed below, each panty liner may comprise several contiguous segments 2, one or more intermediate tear lines 11 will remain within the panty liner after it has been separated from the strip 1. Thus, unlike the absorbent strip 3, the barrier 7 is not perforated at the tear lines 11 since such perforations could result in leakage through such intermediate tear lines.

Figure 3:
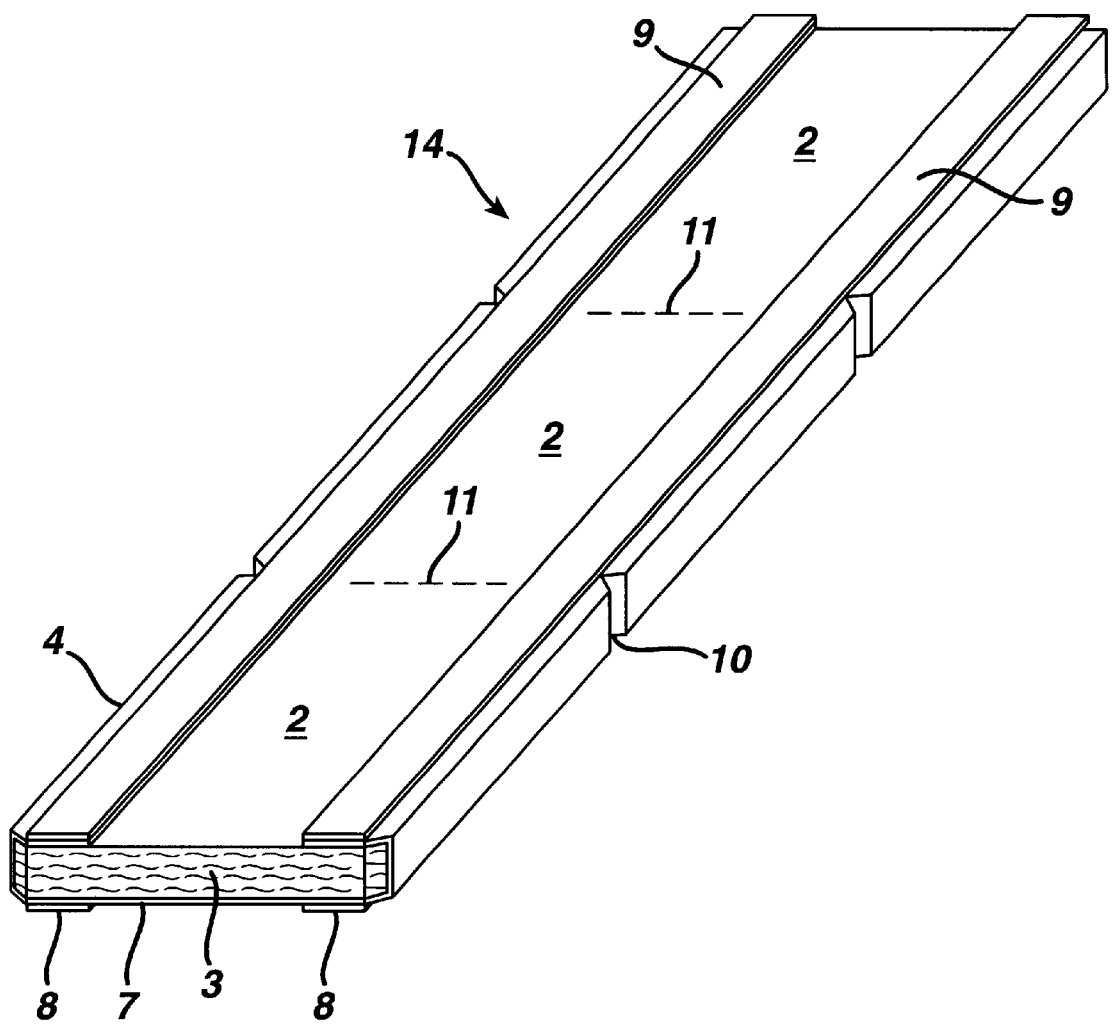
FIG. 3 is an isometric view of a pad after it has been torn from the strip of absorbent product shown in FIG. 1.

According to an important aspect of the current invention, the length L of each segment 2, shown in FIG. 1, is less than that required for a panty liner pad. In fact, the length L should be sufficiently small so that approximately three segments 2 are required to form a standard size panty liner pad 14, shown in FIG. 3. Thus, should the user expect only a small stain on any given day, she will tear off two segments 2 in one piece to form a short panty liner pad. By tearing off three, four or five segments 2 in one piece, the user can create a standard length, long or extra long panty liner pad. In the preferred embodiment, the length L is less than approximately four inches, preferably in the range of approximately one to three inches, most preferably approximately two inches. Moreover, in the preferred embodiment, the overall length of the panty liner strip 1 is at least approximately fifty inches, preferably approximately one hundred to one hundred fifty inches. Most preferably, the overall length is approximately one hundred thirty two inches so that, if the segments 2 are two inches long and a standard size pad is three segments long (i.e., six inches), a single strip 1 will contain a supply of at least twenty two standard size panty liner pads.

As can readily be appreciated, the user is given considerable flexibility in choosing the pad length that will suit her needs on any given day, without the necessity of purchasing pads in varying length. Since the panty liner supply strip 1 is preferentially weakened between each segment, no special dispenser is required to cut the segments from the strip 1, nor need the user carry a pair of scissors.

Figure 4:
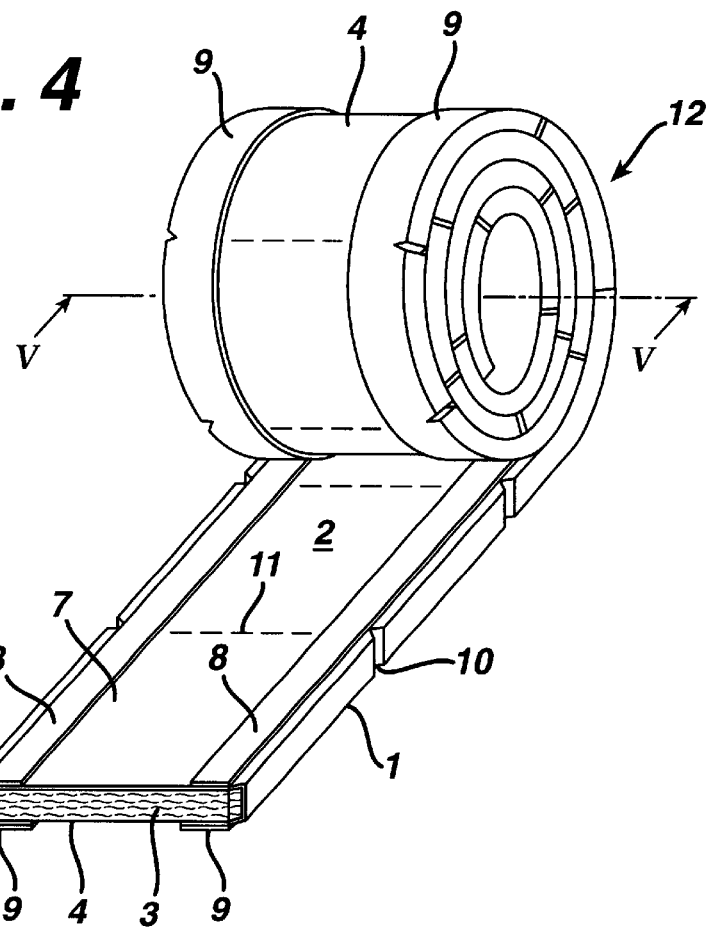
FIG. 4 is an isometric view of the strip of absorbent product shown in FIG. 1 after it has been wrapped into a roll.
Figure 5:
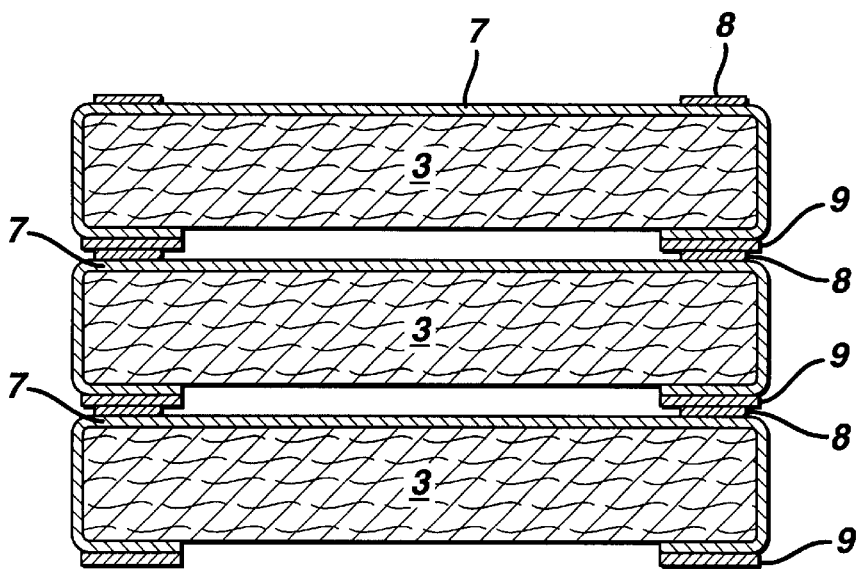
FIG. 5 is a cross-section taken along lines V—V shown in FIG. 4.

According to another important aspect of the current invention, the panty liner supply strip 1 can be wrapped upon itself to form a roll 12, with the body facing surface 4 of the strip in contact with the garment facing surface 16, as shown in FIG. 4. By wrapping the strip 1 so that the garment facing surface 16 formed by the barrier 7 is wrapped upon itself, the strips of adhesive 8 are placed against the release surfaces 9, with the release surfaces being disposed on the outside of the roll 12, as shown in FIGS. 4 and 5. Advantageously, the release surfaces 9 are wider than the strips of pressure sensitive adhesive 8 so as to provide sufficient tolerance to ensure that all of the adhesive will contact a release surface. In the preferred embodiment, each release surface 9 is approximately 0.4 inch wide and each strip of pressure sensitive adhesive 8 is approximately 0.25 inch wide.

As can be appreciated, the pressure sensitive adhesive strips are protected from contamination or inadvertent sticking prior to use without the necessity of release paper. The user merely pulls the panty liner strip 1 from the roll 12 and tears off a sufficient number of segments 2 in one piece to form a panty liner pad to suit her needs on that occasion and applies the pad to an undergarment.

Although the current invention has been discussed with reference to panty liner pads, the invention is also applicable to other types of absorbent products, such as sanitary napkins and incontinence pads. Accordingly, the present invention may be embodied in other specific forms without departing from the spirit or essential attributes thereof and, accordingly, reference should be made to the appended claims, rather than to the foregoing specification, as indicating the scope of the invention.

What is claimed:

1. A supply of absorbent pads for use in absorbing body fluids so as to prevent staining of a user's garment, comprising a longitudinally extending strip of absorbent pad segments, the pad segments having a predetermined uniform interval length of from about 1 to about 3 inches, said strip being tearable into individual absorbent pads without the use of a dispenser having a cutting edge or scissors, said strip of absorbent pad segments having longitudinally extending first and second edges and:

(a) a longitudinally extending body facing surface defined in part by a first major surface of a longitudinally extending strip of absorbent material having a plurality of substantially transverse weakened zones forming preferential tearing lines, said weakened zones spaced at predetermined intervals along said absorbent material strip corresponding to the predetermined interval lengths of said pad segments;

(b) a longitudinally extending fluid impervious barrier strip, wherein a portion of said barrier strip overlies and is adhesively bonded to the absorbent material covering a second major surface, opposite the first major surface of said absorbent material strip and forming a longitudinally extending garment facing surface of said strip of absorbent pad segments, and portions of said barrier strip forming first and second portions of said body facing surface adjacent said first and second longitudinally extending edges, respectively;

(c) a pressure sensitive adhesive disposed on said garment-facing surface of said strip of the absorbent pad segments; and (d) a continuous, longitudinally extending release surface formed on said first and second portions of said body-facing surface formed by said barrier strip, proximate the edges;

wherein said fluid impervious barrier strip forms a fluid barrier which prevents fluid leakage during use of said absorbent pads, said longitudinally extending strip of absorbent pad segments is wrapped around itself into a roll to place said pressure sensitive adhesive into contact with at least a portion of said release surface and said individual absorbent pads are formed of a plurality of absorbent pad segments.

2. The supply of absorbent pads according to claim 1 wherein the barrier strip extends along a length of said longitudinally extending strip of absorbent material.

3. The supply of absorbent pads according to claim 1, wherein each of said tearing lines comprises perforations formed in said absorbent material strip.

4. The supply of absorbent pads according to claim 1, wherein said pressure sensitive adhesive is disposed along at least a portion of said garment facing surface in each of said absorbent pad segments.

5. The supply of absorbent pads according to claim 1, wherein the pressure sensitive adhesive extends longitudinally on said garment facing surface along a length of said strip of absorbent material.

6. The supply of absorbent pads according to claim 1, wherein said release surface is formed by coating a portion of said barrier strip forming first and second portions, of said body facing surface with a release agent.

7. The supply of absorbent pads according to claim 1, wherein said release surface comprises silicone.

8. The supply of absorbent pads according to claim 1, wherein said first surface of said absorbent material strip forms a third portion of said body facing surface disposed between said first and second portions.

9. The supply of absorbent pads according to claim 1, wherein said garment-facing and body-facing surfaces have a common length.

10. The supply of absorbent pads according to claim 1, wherein said longitudinally extending strip of absorbent pad segments is at least fifty inches long.

11. A method of making absorbent pads, comprising the steps of:
   a) forming a longitudinally extending strip of an absorbent element, said absorbent element having first and second opposed longitudinally extending surfaces, longitudinally extending edges, and a plurality of substantially transverse weakened zones forming preferential tearing lines, said weakened zones spaced at predetermined, uniform intervals about 1 to about 3 inches along said absorbent element to define absorbent pad segments therebetween;
   (b) overlaying said second surface, said longitudinally extending edges, and a portion of said first surface, with a fluid impervious barrier strip;
   (c) depositing a pressure sensitive adhesive on at least a portion of said barrier strip overlaying said second surface;
   (d) forming a release surface on at least a portion of said barrier strip overlaying said portion of said first surface; and
   (e) wrapping said strip of absorbent element around itself into a roll so as to place said pressure sensitive adhesive into contact with at least a portion of said release surface.

12. The method of making absorbent pads according to claim 11, wherein the step of forming said release surface comprises forming said release surface along a length of said at least a portion of said barrier strip overlaying said portion of said first surface.

13. The method of making absorbent pads according to claim 12, wherein the step of depositing the pressure sensitive adhesive comprises depositing said pressure sensitive adhesive along a length of said at least a portion of said barrier strip overlaying said second surface.

14. A supply of absorbent pads for use in absorbing body fluids so as to prevent staining of a user's garment, comprising a longitudinally extending strip of absorbent pad segments, the pad segments having a predetermined uniform interval length of from about 1 to about 3 inches, said strip being tearable into individual absorbent pads without the use of a dispenser having a cutting edge or scissors, said strip of absorbent pad segments having longitudinally extending first and second edges and:

a) a longitudinally extending body facing surface defined in part by a first major surface of a longitudinally extending strip of absorbent material having a plurality of substantially transverse weakened zones forming preferential tearing lines, said weakened zones spaced at predetermined intervals along said absorbent material strip corresponding said predetermined interval length of said pad segments;

b) a longitudinally extending fluid impervious barrier strip, wherein a portion of said barrier strip overlies and is adhesively bonded to the absorbent material covering a second major surface, opposite the first major surface of said absorbent material strip and forming a longitudinally extending garment facing surface of said strip of absorbent pad segments, and portions of said barrier strip forming first and second portions of said body facing surface adjacent said first and second longitudinally extending edges, respectively;

c) a pressure sensitive adhesive disposed on said garment-facing surface of said strip of the absorbent pad segments; and d) a continuous, longitudinally extending release surface formed on said first and second portions of said body-facing surface formed by said barrier strip, proximate the edges, wherein said release surface being wider than said pressure sensitive adhesive;

wherein said fluid impervious barrier strip forms a fluid barrier, which prevents fluid leakage during use of said absorbent pads, said longitudinally extending strip of absorbent pad segments is wrapped around itself into a roll to place said pressure sensitive adhesive into contact with at least a portion of said release surface and said individual absorbent pads are formed of a plurality of absorbent pad segments.

15. A method of making absorbent pads, comprising the steps of:

a) forming a longitudinally extending strip of an absorbent element, said absorbent element having first and second opposed longitudinally extending surfaces longitudinally extending edges, and a plurality of substantially transverse weakened zones forming preferential tearing lines, said weakened zones spaced at predetermined, uniform intervals about 1 to about 3 inches along said absorbent element to define absorbent pad segments therebetween;

b) overlaying said second surface, said longitudinally extending edges, and a portion of said first surface, with a fluid impervious barrier strip;

c) depositing a pressure sensitive adhesive on at least a portion of said barrier strip overlaying said second surface;

d) forming a release surface on at least a portion of said barrier strip overlaying said portion of said first surface, wherein said release surface is wider than said pressure sensitive adhesive; and e) wrapping said strip of absorbent element around itself into a roll so as to place said pressure sensitive adhesive into contact with at least a portion of said release surface.

* * * * *

UNITED STATES PATENT AND TRADEMARK OFFICE
CERTIFICATE OF CORRECTION

PATENT NO.    : 6,254,582 B1                                                    Page 1 of 1
DATED         : July 3, 2001
INVENTOR(S)   : Kathleen Denise O'Donnell and Thomas Joseph Luceri It is certified that error appears in the above-identified patent and that said Letters Patent is hereby corrected as shown below:

<u>Column 7,</u>
Line 22, please delete ","

Signed and Sealed this

Thirtieth Day of December, 2003

JAMES E. ROGAN
*Director of the United States Patent and Trademark Office*